United States Patent [19]

DeMartino et al.

[11] Patent Number: 4,892,682

[45] Date of Patent: Jan. 9, 1990

[54] AZOMETHINE COMPOSITIONS HAVING NONLINEAR OPTICAL PROPERTIES

[75] Inventors: Ronald N. DeMartino, Wayne; Hyun-Nam Yoon, New Providence; James B. Stamatoff, Westfield, all of N.J.

[73] Assignee: Hoechst Celanese Corporation, Sommerville, N.J.

[21] Appl. No.: 326,115

[22] Filed: Mar. 20, 1989

Related U.S. Application Data

[62] Division of Ser. No. 927,990, Nov. 7, 1986.

[51] Int. Cl.$^4$ .............................................. G02B 5/22
[52] U.S. Cl. .................................... 252/589; 252/600; 252/582
[58] Field of Search ............... 252/582, 586, 588, 589, 252/600

[56] References Cited

U.S. PATENT DOCUMENTS 3,697,595 10/1972 Clecak et al. .................. 260/566 R

OTHER PUBLICATIONS

Williams, D. J., Angew. Chem. Int. Edl. Eng. 23, 1984, 690.
Shtykov, N. M. et al., Mol. Cryst. Liq. Cryst. 124, 1985, 379.
Tweig, R. J., Jain, K. in Nonlinear Properties of Organic and Polymeric Materials, Williams, D. J., ed. ACS Washington, DC, 1983, Chapter 3.

Primary Examiner—Teddy S. Gron
Assistant Examiner—Richard Treanor
Attorney, Agent, or Firm—DePaoli & O'Brien

[57] ABSTRACT

In one embodiment this invention provides a novel class of azomethine compounds which exhibit nonlinear optical response, such as 4-(4-dimethylaminobenzylideneamino)-4'- nitrostilbene:

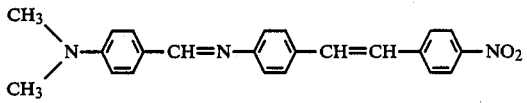

4 Claims, No Drawings

AZOMETHINE COMPOSITIONS HAVING NONLINEAR OPTICAL PROPERTIES

This invention was made with Government support under Contract Number F49620-85-0047 awarded by the Department of Defense. The Federal Government has certain rights in this invention.

This application is a division of application Ser. No. 927,990 filed 11/7/86.

BACKGROUND OF THE INVENTION

It is known that organic and polymeric materials with large delocalized $\pi$-electron systems can exhibit nonlinear optical response, which in many cases is a much larger response than by inorganic substrates.

In addition, the properties of organic and polymeric materials can be varied to optimize other desirable properties, such as mechanical and thermoxidative stability and high laser damage threshold, with preservation of the electronic interactions responsible for nonlinear optical effects.

Thin films of organic or polymeric materials with large second-order nonlinearities in combination with silicon-based electronic circuitry have potential as systems for laser modulation and deflection, information control in optical circuitry, and the like.

Other novel processes occurring through third-order nonlinearity such as degenerate four-wave mixing, whereby real-time processing of optical fields occurs have potential utility in such diverse fields as optical communications and integrated circuit fabrication.

Nonlinear optical properties of organic and polymeric materials was the subject of a symposium sponsored by the ACS division of Polymer Chemistry at the 18th meeting of the American Chemical Society, September 1982. Papers presented at the meeting are published in ACS Symposium Series 233, American Chemical Society, Washington, D.C. 1983.

The above-recited publications are incorporated herein by reference.

Of general interest with respect to the present invention is prior art relating to azomethine derivatives, such as those described in U.S. Pat. Nos. 3,041,165; 3,253,022; 3,483,131; 3,697,595; 3,742,054; 3,872,140; 3,968,159; 3,973,830; 4,122,026; 4,173,544; 4,297,502; and 4,370,502.

There is continuing research effort to develop new nonlinear optical organic systems for prospective novel phenomena and devices adapted for laser frequency conversion, information control in optical circuitry, light valves and optical switches. The potential utility of organic materials with large second-order and third-order nonlinearities for very high frequency application contrasts with the bandwidth limitations of conventional inorganic electrooptic materials.

Accordingly, it is an object of this invention to provide organic compositions which are characterized by a delocalized conjugated $\pi$-electron system which can exhibit nonlinear optical response.

It is another object of this invention to provide azomethine derivatives which exhibit nonlinear optical response.

It is a further object of this invention to provide high performance nonlinear optical media and devices.

Other objects and advantages of the present invention shall become apparent from the accompanying description and examples.

DESCRIPTION OF THE INVENTION

One or more objects of the present invention are accomplished by the provision of an azomethine composition corresponding to the formula:

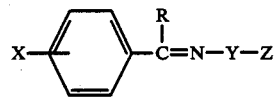

where X is an electron-donating substituent; Z is an electron-withdrawing substituent; R is hydrogen or a $C_1$–$C_4$ alkyl substituent; and Y is a substituent selected from

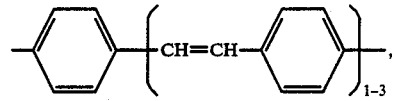

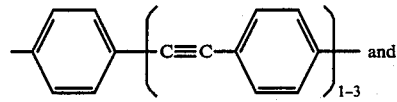

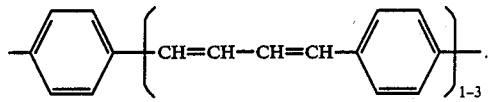

The term "electron-donating" as employed herein refers to organic substituents which contribute $\pi$-electrons when the conjugated electronic structure is polarized by the input of electromagnetic energy.

The term "electron-withdrawing" as employed herein refers to electronegative organic substituents which attract $\pi$-electrons when the conjugated electronic structure is polarized by the input of electromagnetic energy.

Illustrative of electron-donating X groups are amino, alkyl, alkoxy, alkylthio, hydroxy, thiolo, acyloxy, vinyl, halo, and the like.

Illustrative of electron-withdrawing substituents as represented by Z in the above formula are nitro, haloalkyl, cyano, acyl, alkoxycarbonyl, alkoxysulfonyl, and the like.

Illustrative of $C_1$–$C_4$ alkyl R substituents are methyl, ethyl, propyl, isopropyl, butyl, isobutyl and 2-butyl.

The Y structures as represented in the formula can have aromatic ring substituents such as alkyl, alkoxy, halo, and the like.

A present invention azomethine composition has nonlinear optical properties, e.g., a second order nonlinear optical susceptibility $\beta$ of at least about $1 \times 10^{-30}$ esu as measured at 1.91 $\mu$m excitation wavelength.

In another embodiment this invention provides an azomethine composition corresponding to the formula:

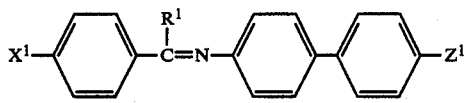

where $X^1$ is —$NR^2R^2$, —$OR^2$ or —$SR^2$; $R^1$ is hydrogen or methyl; $R^2$ is hydrogen or a $C_1$–$C_{20}$ alkyl group; and $Z^1$ is —$NO_2$, —$CN$ or —$CF_3$.

Illustrative of $C_1$–$C_{20}$ alkyl $R^2$ groups are methyl, butyl, octyl, 2-decyl, dodecyl, octadecyl and eicosyl.

In another embodiment this invention provides an azomethine composition corresponding to the formula:

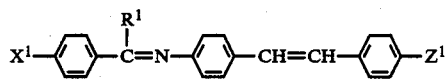

where $X^1$ is —$NR^2R^2$, —$OR^2$ or —$SR^2$; $R^1$ is hydrogen or methyl; $R^2$ is hydrogen or a $C_1$–$C_{20}$ alkyl group; and $Z^1$ is —$NO_2$, —$CN$ or —$CF_3$.

In another embodiment this invention provides an azomethine composition corresponding to the formula:

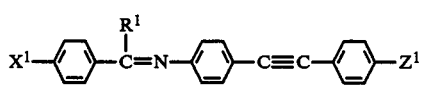

where $X^1$ is —$NR^2R^2$, —$OR^2$ or —$SR^2$; $R^1$ is hydrogen or methyl; $R^2$ is hydrogen or a $C_1$–$C_{20}$ alkyl group; and $Z^1$ is —$NO_2$, —$CN$ or —$CF_3$.

In another embodiment this invention provides an azomethine composition corresponding to the formula:

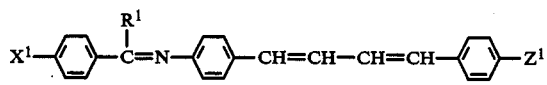

where $X^1$ is —$NR^2R^2$, —$OR^2$ or —$SR^2$; $R^1$ is hydrogen or methyl; $R^2$ is hydrogen or a $C_1$–$C_{20}$ alkyl group; and $Z^1$ is —$NO_2$, —$CN$ or —$CF_3$.

In another embodiment this invention provides a nonlinear optical medium in the form of a transparent solid which is a blend of constituents comprising (1) a host thermoplastic polymer; and (2) a guest organic compound corresponding to the formula:

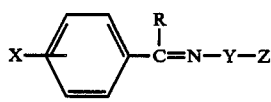

where X is an electron-donating substituent; Z is an electron-withdrawing substituent; R is hydrogen or a $C_1$–$C_4$ alkyl substituent; and Y is a substituent selected from

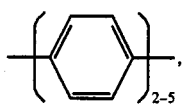

-continued

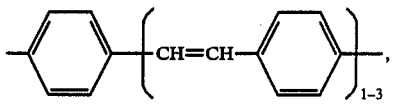

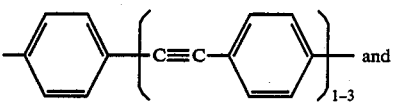

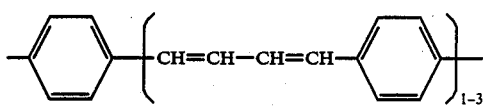

The guest azomethine compound in the organic blend defined above will comprise about 5–30 weight percent of the total weight of the blend constituents of the transparent solid.

When a nonlinear optical medium as defined above is noncentrosymmetric in molecular and unit cell configurations, then the transparent solid exhibits second order nonlinear optical response. If the nonlinear optical medium is centrosymmetric, then the transparent solid exhibits third order nonlinear optical response.

In another embodiment this invention provides a nonlinear optical medium in the form of a transparent solid which is a blend of constituents comprising (1) a host thermoplastic polymer; and (2) a guest organic compound corresponding to the formula:

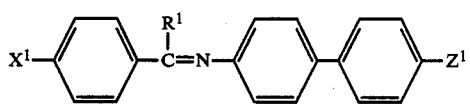

where $X^1$ is —$NR^2R^2$, —$OR^2$ or —$SR^2$; $R^1$ is hydrogen or methyl; $R^2$ is hydrogen or a $C_1$–$C_{20}$ alkyl group; and $Z^1$ is —$NO_2$, —$CN$ or —$CF_3$.

In another embodiment this invention provides a nonlinear optical medium in the form of a transparent solid which is a blend of constituents comprising (1) a host thermoplastic polymer; and (2) a guest organic compound corresponding to the formula:

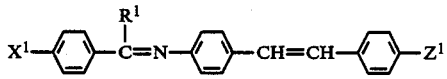

where $X^1$, $R^1$ and $Z^1$ are as previously defined.

In another embodiment this invention provides a nonlinear optical medium in the form of a transparent solid which is a blend of constituents comprising (1) a host thermoplastic polymer; and (2) a guest organic compound corresponding to the formula:

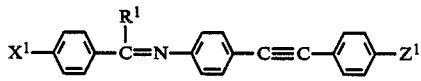

where $X^1$, $R^1$ and $Z^1$ are as previously defined.

In another embodiment this invention provides a nonlinear optical medium in the form of a transparent solid which is a blend of constituents comprising (1) a host thermoplastic polymer; and (2) a guest organic compound corresponding to the formula:

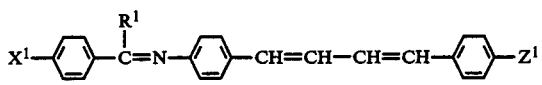

where $X^1$, $R^1$ and $Z^1$ are as previously defined.

In a further embodiment this invention provides an optical light switch or light modulator device with an organic nonlinear optical component consisting of a transparent solid medium which is a blend of constituents comprising (1) a host thermoplastic polymer; and (2) a guest organic compound corresponding to the formula:

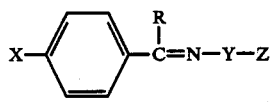

where X, R, Y and Z are as previously defined.

An invention light switch or light modulator device typically will have a transparent solid medium in which the guest azomethine molecular and the host polymer, e.g., a thermotropic liquid crystalline polymer, have an external field-induced molecular orientation.

The term "transparent" as employed herein refers to an optical medium which is transparent or light transmitting with respect to incident fundamental light frequencies and created light frequencies. In a nonlinear optical device, a present invention nonlinear optical medium is transparent to both the incident and exit light frequencies.

Suitable thermoplastic polymers which can be employed as a constituent of the transparent solid blends defined above include poly(meth)acrylates, polyacrylamides, liquid crystalline polymers, and the like.

A preferred type of host thermoplastic polymer is a thermoplastic liquid crystalline polymer having a comb structure of mesogenic sidechains which comprise at least about 25 weight percent of the polymer, wherein the polymer has a glass transition temperature above about 40° C., and the mesogens exhibit nonlinear optical response.

The main chain of the liquid crystalline polymer can consist of structures such as polyvinyl, polysiloxane, polyoxyalkylene, polyester, polyamide, and the like.

The liquid crystalline polymer typically will exhibit a smectic and/or nematic mesophase.

Illustrative of a preferred host thermoplastic polymer is one which is characterized by a recurring monomeric unit corresponding to the formula:

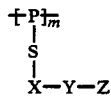

where P is a polymer main chain unit; m is an integer of at least 3; S is a flexible spacer group having a linear chain length of between about 1-25 atoms; X is —NR—, —O— or —S—; R is hydrogen or a $C_1$-$C_4$ alkyl group; Y is

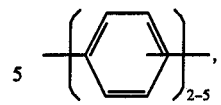

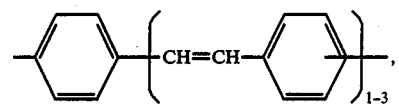

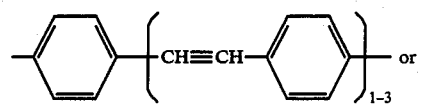

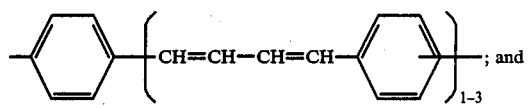

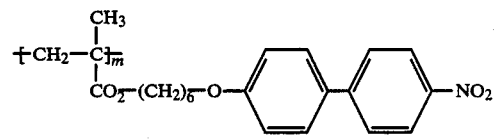

Z is an electron-withdrawing group.

A sidechain liquid crystalline polymer of the above formula is illustrated by poly[6-(4-nitrobiphenyloxy)-hexyl methacrylate]:

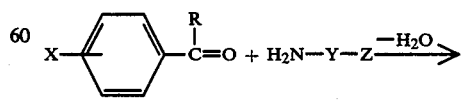

The preparation of sidechain liquid crystalline polymers which exhibit nonlinear optical response is described in copending patent application Ser. No. 822,090, filed Jan. 24, 1986; incorporated herein by reference.

A present invention transparent nonlinear optical medium can be prepared by dissolving the guest azomethine and host polymer components in a solvent such as toluene or N,N-dimethylformamide and spin coating the solution on the surface of a transparent substrate such as optical glass to form a thin coating. A nonlinear optical medium also can be shaped by casting or molding a melt phase of the organic blend to form a film, lens, prism, and the like.

The optical medium may be optically isotropic or anisotropic depending on the application of an external field.

Synthesis Of Azomethine Compounds

A general procedure for the preparation of a present invention azomethine compound is illustrated by the following flow diagram:

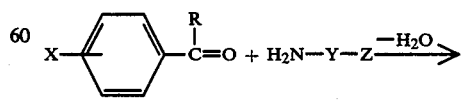

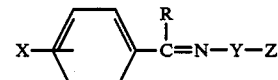

Illustrative of the synthesis procedure is the preparation of 4-(4-methylthiobenzylideneamino)-411-trifluoromethyltriphenyl:

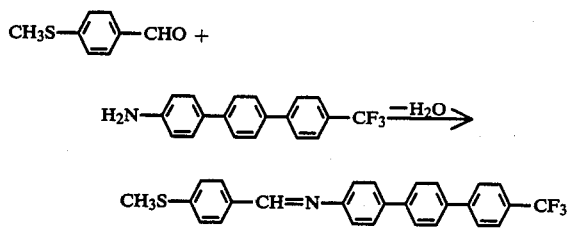

Nonlinear Optical Properties

The fundamental concepts of nonlinear optics and their relationship to chemical structures can be expressed in terms of dipolar approximation with respect to the polarization induced in an atom or molecule by an external field.

As summarized in the ACS Symposium Series 233 (1983) listed hereinabove in the Background Of The Invention section, the fundamental equation (1) below describes the change in dipole moment between the ground state $\mu_g$ and an excited state $\mu_e$ expressed as a power series of the electric field E which occurs upon interaction of such a field, as in the electric component of electromagnetic radiation, with a single molecule. The coefficient $\alpha$ is the familiar linear polarizability, $\beta$ and $\gamma$ are the quadratic and cubic hyperpolarizabilities, respectively. The coefficients for these hyperpolarizabilities are tensor quantities and therefore highly symmetry dependent. Odd order coefficients are nonvanishing for all structures on the molecular and unit cell level. The even order coefficients such as $\beta$ are zero for those structures having a center of inversion symmetry on the molecular and/or unit cell level.

Equation (2) is identical with (1) except that it describes a macroscopic polarization, such as that arising from an array of molecules in an organic blend domain:

$$\Delta\mu = \mu_e - \mu_g = \alpha E + \beta EE + \gamma EEE + \ldots \qquad (1)$$

$$P = P_0 + \chi^{(1)}E + \chi^{(2)}EE + \chi^{(3)}EEE + \ldots \qquad (2)$$

Light waves passing through an array of molecules can interact with them to produce new waves. This interaction may be interpreted as resulting from a modulation in refractive index or alternatively as a nonlinearity of the polarization. Such interaction occurs most efficiently when certain phase matching conditions are met, requiring identical propagation speeds of the fundamental wave and the harmonic wave.

A present invention thermoplastic guest/host medium typically is optically transparent and exhibits hyperpolarization tensor properties such as second harmonic generation.

These theoretical considerations are elaborated by Garito et al in chapter 1 of the ACS Symposium Series 233 (1983); and by Lipscomb et al in J. Chem., Phys., 75, 1509 (1981), incorporated by reference. See also Lalama et al, Phys. Rev., A20, 1179 (1979); and Garito et al, Mol., Cryst. and Liq. Cryst., 106, 219 (1984); incorporated by reference.

Field-induced Macroscopic Nonlinearity

The term "external field" as employed herein refers to an electric, magnetic or mechanical stress field which is applied to a substrate of mobile organic molecules, to induce dipolar alignment of the molecules parallel to the field.

The electronic origins of nonlinear optical effects in organic $\pi$-electronic systems is reviewed by D. J. Williams in Angew. Chem., Int. Ed. Engl., 23, 690 (1984); incorporated herein by reference.

As described in the review article, a technique has been developed for measuring $\beta$ without necessitating the incorporation of the molecule into noncentrosymmetric crystal structures. In this technique, called electric field-induced second-harmonic generation (EFISH), a strong DC electric field is applied to a liquid or a solution of the molecules of interest in order to remove the orientational averaging by statistical alignment of molecular dipoles in the medium. The induced second-order nonlinearity can then produce a signal at $2\omega$, from which $\beta$ can be extracted.

A schematic diagram of experimental system for measurement of $\beta$ by the EFISH technique is presented in the review article. As illustrated in the published diagram, the 1.06 $\mu$m output of a $Nd^{3+}$:YAG laser is split and directed into a sample and a reference cell. The sample cell is translated by a stepped-motor-controlled stage across the beam. The laser pulse is synchronized with a high-voltage DC pulse to induce harmonic generation in the cell. The 0.53 $\mu$m radiation is separated from the 1.06 $\mu$m pump beam by filters and a monochromator, and the harmonic intensity is detected by a photomultiplier tube. The signal-to-noise ratio can be improved with a boxcar averager. The reference beam is directed into a crystal such as quartz, whose second-order properties are well known, so that fluctuations in beam intensity can be readily corrected in the output data. The value of the nonlinear coefficient is obtained from the ratio of the signals of the sample cell and a reference material such as quartz or $LiNbO_3$ with known $\chi^{(2)}$.

A present invention thermoplastic guest/host medium is adapted to exhibit the external field-induced macroscopic nonlinearity required for second-order harmonic generation.

A guest/host medium which is isotropic exhibits Kerr effect response and third-order nonlinear optical susceptibility $\chi^{(3)}$. If a guest/host medium is oriented, it exhibits enhanced Kerr effect and $\chi^{(3)}$ responses.

A guest/host medium which is poled in a DC field and is isotropic exhibits Pockels effect response and second-order nonlinear optical susceptibility $\chi^{(2)}$. If the DC poled guest/host medium is oriented, then the medium exhibits enhanced $\chi^{(2)}$ response.

The following examples are further illustrative of the present invention. The components and specific ingredients are presented as being typical, and various modifications can be derived in view of the foregoing disclosure within the scope of the invention.

EXAMPLE I

This Example illustrates the preparation of azomethine compounds in accordance with the present invention.

A. 4-(4-hydroxybenzylideneamino)-4'-nitrodiphenyl

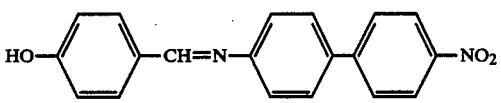

A reactor is charged with toluene (100 mls), 4-amino-4'-nitrobiphenyl (4.28 g, 0.02 M), p-hydroxybenzaldehyde (2.44 g, 0.02 M), and 0.1 g of p-toluenesulfonic acid. The solution is heated to reflux temperature, and the heating is continued for a period of about 20 hours, with continuous removal of water with a Dean-Stark trap.

The solvent is evaporated under vacuum, and the residual solid is recrystallized from 50/50 ethanol/toluene to yield the azomethine product, m.p. 165°-180° C.

The azomethine product can exhibit a second order nonlinear susceptibility $\beta$ of at least about $1 \times 10^{-30}$ esu as measured at 1.91 μm excitation wavelength.

B. 4-(4-methoxybenzylideneamino)-4'-cyanobiphenyl

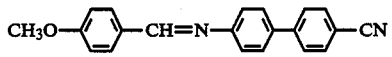

Following the procedure described above, 4-methoxybenzaldehyde is reacted with 4-amino-4'-cyanobiphenyl to yield the azomethine product.

C. 4-(4-dimethylaminobenzylideneamino)-4'-nitrodiphenyl

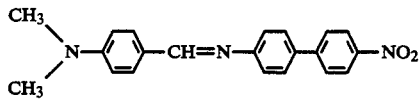

Following the procedure described above, 4-dimethylaminobenzaldehyde is reacted with 4-amino-4'-nitrobiphenyl to yield the azomethine product.

D. 4-(4-dimethylaminobenzylideneamino)-4'-nitrostilbene

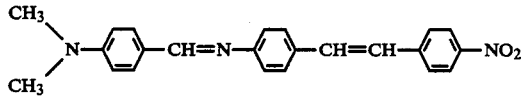

Following the procedure described above, p-dimethylaminobenzaldehyde is reacted with 4-amino-4'-nitrostilbene to yield the azomethine product.

E. 4-(4-dibutylaminobenzylideneamino)-4'-trifluoromethyldiphenylacetylene

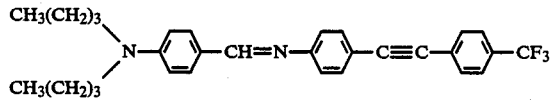

Following the procedure described above, p-dibutylaminobenzaldehyde is reacted with 4-amino-4'-trifluoromethylacetylene.

EXAMPLE II

This Example illustrates a poling procedure for producing a second order nonlinear optical medium of a guest azomethine compound and a host side chain liquid crystalline polymer in accordance with the present invention.

A. Poling Cell Construction

A poling cell is constructed from electrically conductive glass plates, such as Corning Glass EC-2301 or Donnelly Mirror PD 5007-7. The glass plates are washed with sulfuric acid, isopropanol, 1-dodecanol, and isopropanol, with a distilled water rinse between each washing step.

The poling cell is a sandwich type cell in which the conductive glass surfaces are in facing proximity and are separated by a polyimide film of approximately 25 micrometer thickness. A thin layer of epoxy adhesive is applied on the surfaces of the polyimide film to hold the glass plates.

After the epoxy is completely cured, the cell is washed with isopropanol and rinsed with distilled water. After drying, the cell is stored in a dry box.

B. Filling The Poling Cell

Poly[6-(4-nitrobiphenyloxy)hexyl methacrylate]-doped with 10 percent by weight of 4-(4-hydroxybenzylideneamino)4'-nitrodiphenyl is placed in a vacuum oven and maintained in a melt phase at a temperature of about 120° C. for about 4 hours to eliminate entrained air bubbles from the polymer melt.

The liquid crystalline polymer melt is introduced into the space between the glass plates by charging a drop of the polymer melt to one of the openings of the poling cell space and placing the cell assembly in a vacuum oven maintained at a temperature approximately 10° C. above the clearing temperature of the liquid crystalline polymer. The cell space fills gradually by capillary action. The space filling period is about 4 hours for a 0.5 cm long space.

C. Electric Field-Induced Orientation

Two lead wires are attached to each of the conductive glass surfaces using electrically conductive epoxy adhesive. The poling assembly is placed in a microscope hot stage (Mettler FP-82 with FP-80 Central Processor), and the sample is observed with a polarizing microscope (Leitz Ortholux Pol) for alignment.

The microscope is switched into a photodiode (Mettler Photometer No. 17517) to record the change of light intensity upon application of an electric field. The two lead wires are connected to an AC voltage amplifier (Electro-Optic Developments LA10A), which amplifies the voltage signal from a signal generator (Hewlett-Packar No. 3310B).

The poling cell first is heated to 85° C. to bring the liquid crystalline polymer component to the isotropic phase. : The assembly then is cooled at a rate of 0.2° C./min. until the photodiode signal registers an abrupt increase which indicates that the melt has undergone a transition into a liquid crystalline phase. The temperature is further lowered by 2° C. and then maintained at this temperature.

The AC voltage source is set at 500 V, and the frequency is set at 2000 Hz. The power to the poling cell is turned on to apply an electric field across the doped polymer sample. The field strength is calculated to be approximately $2 \times 10^5$ V/cm. About three seconds after the electric field is applied, the photodiode signal drops close to the baseline, indicating that orientation development induced by the electric field is completed. At this point, the cooling is resumed until the temperature reaches 35° C., and the poling assembly is disconnected from the power source.

When the poling assembly is removed from the microscope hot stage, by visual observation the melt phase in the cell space is transparent. This is an indication that the molecular orientation is uniform and homogeneous throughout the sample. Orientation of the sample is further ascertained utilizing a wide angle X-ray diffraction technique, and the Hermann's orientation factor of the sample is approximately 0.9.

D. High Field Poling For Symmetry Control

The oriented doped polymer sample is subjected further to a high electric field to develop a noncentrosymmetric orientation of nonlinear optical moieties which are a part of the side chains of the polymer, and orientation of the guest azomethine molecules.

The poling cell assembly is heated to approximately 5° C. below the glass transition temperature of the polymer. Then the lead wires of the poling assembly are connected to a DC voltage source (Kepco OPS-3500) and the voltage is turned up slowly until it reaches 2000 V. At this point, the electric field strength across the sample is about $8 \times 10^5$ V/cm. The sample is maintained at this field strength level for 2 minutes, and then the voltage source is disconnected. A noncentrosymmetrically oriented liquid medium of host crystalline polymer and guest azomethine compound is obtained when the cell sample is cooled.

The noncentrosymmetry of the sample is determined from the thermally stimulated electrical discharge measurement. Orientation is determined by small and large angle X-ray diffraction measurement. The Hermann's orientation function from the X-ray measurement is approximately 0.6–0.8.

From the measurements, there is an indication that a major proportion of the nonlinear optical moieties are aligned parallel to the electric field direction, and the rest are oriented antiparallel to the electric field direction.

What is claimed is:

1. A nonlinear optical medium in the form of a transparent solid which is a blend of constituents comprising (1) a host thermoplastic polymer; and (2) a guest organic compound corresponding to the formula:

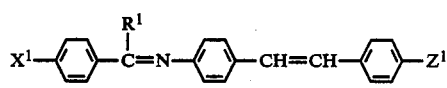

where $X^1$ is $-NR^2R^2$, $-OR^2$ or $-SR^2$; $R^1$ is hydrogen or methyl; $R^2$ is hydrogen or a $C_1-C_{20}$ alkyl group; and $Z^1$ is $-NO_2$, $-CN$ or $-CF_3$.

2. A nonlinear optical medium in accordance with claim 1 wherein the thermoplastic polymer is a liquid crystalline polymer.

3. A nonlinear optical medium in accordance with claim 1 wherein the transparent solid is noncentrosymmetric and exhibits second order nonlinear optical response.

4. A nonlinear optical medium in accordance with claim 1 wherein the transparent solid is centrosymmetric and exhibits third order nonlinear optical response.

* * * * *